US00PP12100P2

(12) United States Plant Patent
Flemer, III

(10) Patent No.: US PP12,100 P2
(45) Date of Patent: Sep. 18, 2001

(54) *HAMAMELIS VIRGINIANA* PLANT NAMED 'NOVEMBER GLOW'

(75) Inventor: William Flemer, III, Allentown, NJ (US)

(73) Assignee: Treesearch, Allentown, NJ (US)

( * ) Notice: Subject to any disclaimer, the term of this patent is extended or adjusted under 35 U.S.C. 154(b) by 0 days.

(21) Appl. No.: 09/573,836

(22) Filed: May 18, 2000

(51) Int. Cl.[7] ..... A01H 5/00
(52) U.S. Cl. ..... Plt./226
(58) Field of Search ..... Plt./226

*Primary Examiner*—Bruce R. Campell
*Assistant Examiner*—Susan B. McCormick
(74) *Attorney, Agent, or Firm*—James A. Lucas; Driggs, Lucas, Brubaker & Hogg Co., LPA

(57) ABSTRACT

A new cultivar of *Hamamelis virginiana* characterized by its exceptionally large and abundant flowers borne on large, dense clusters closely spaced on slender twigs.

2 Drawing Sheets

BACKGROUND OF THE INVENTION

This invention relates to a Hamamelis which is a product of crossing a seed parent *Hamamelis virginiana* (not patented); with an unknown pollen parent. The plant was discovered in bloom in 1989 in a row of seedlings grown from seed of the *Hamamelis virginiana* sown in 1984. I first asexually reproduced the plant by means of grafting on *Hamamelis virginiana* seedlings at Plainsboro Twp. in New Jersy in February of 1992. Additional generations were grown in Plainsboro Twp., N.J. I have observed the plants thus produced and find that the characteristics initially observed are in fact reproduced in successive generations.

The Hamamelis family includes a varied and diversified group of shrubs grown for their ornamental value. They are appreciated for their small yellow or red flowers that have a distinct fragrance when fully opened. The fruit is pod like and dry at maturity, and is characterized by its ability to split at maturity with explosive force, flinging seeds up to 40 feet from the plant.

BRIEF SUMMARY OF THE INVENTION

This new shrub was noticed in a row of Hamamelis seedling-grown plants because it was so showy in bloom, the flowers being borne in large, dense clusters closely spaced on the slender twigs. It was so heavily flowered that it stood out prominently from all of its sibling shrubs. Plants grafted from scions of the mother plant bear the same large and very abundant flowers.

DESCRIPTION OF THE DRAWINGS

This new variety of Hamamelis is illustrated by the accompanying photographic drawing and depicts the plant by the best possible color representation using color photography. All of the color definitions in the specification have been taken from the Munsell Color Chart (hereinafter referred to as 'Munsell'). While the colors depicted are believed to be of a high level of color fidelity, the coloration of this plant should be understood to be approximate and somewhat variable as a function of climate and the cultural conditions and horticultural practices of the grower. For example, the leaf coloration may vary depending on the composition and the concentration of fertilizer that may be applied to the plant. Furthermore, the colors depicted are as close to the actual coloration of the plant as is possible to attain in a photographic illustration of this quality. However, due to factors such as light reflectance, minor differences in coloration may appear.

BOTANICAL DESCRIPTION

Figure 1:
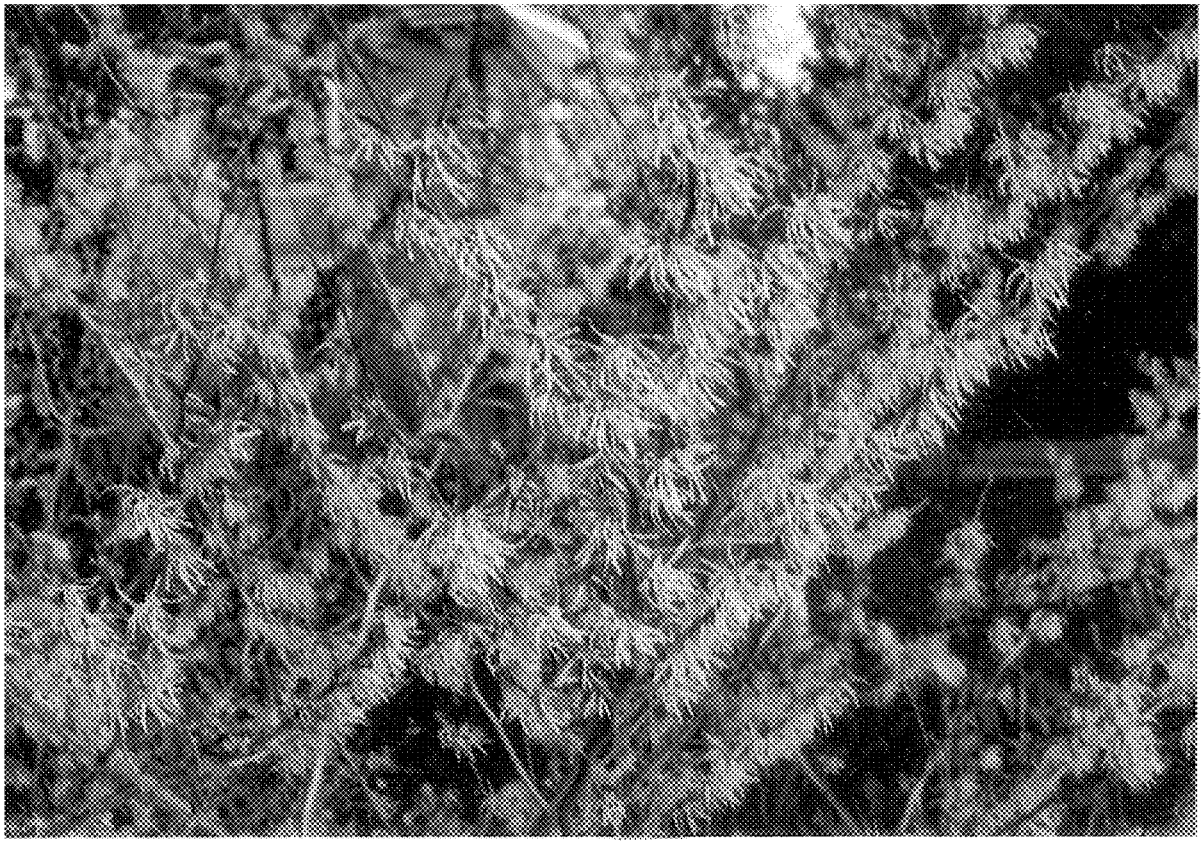
FIG. 1 is a view showing a close-up of the flowers.
Figure 2:
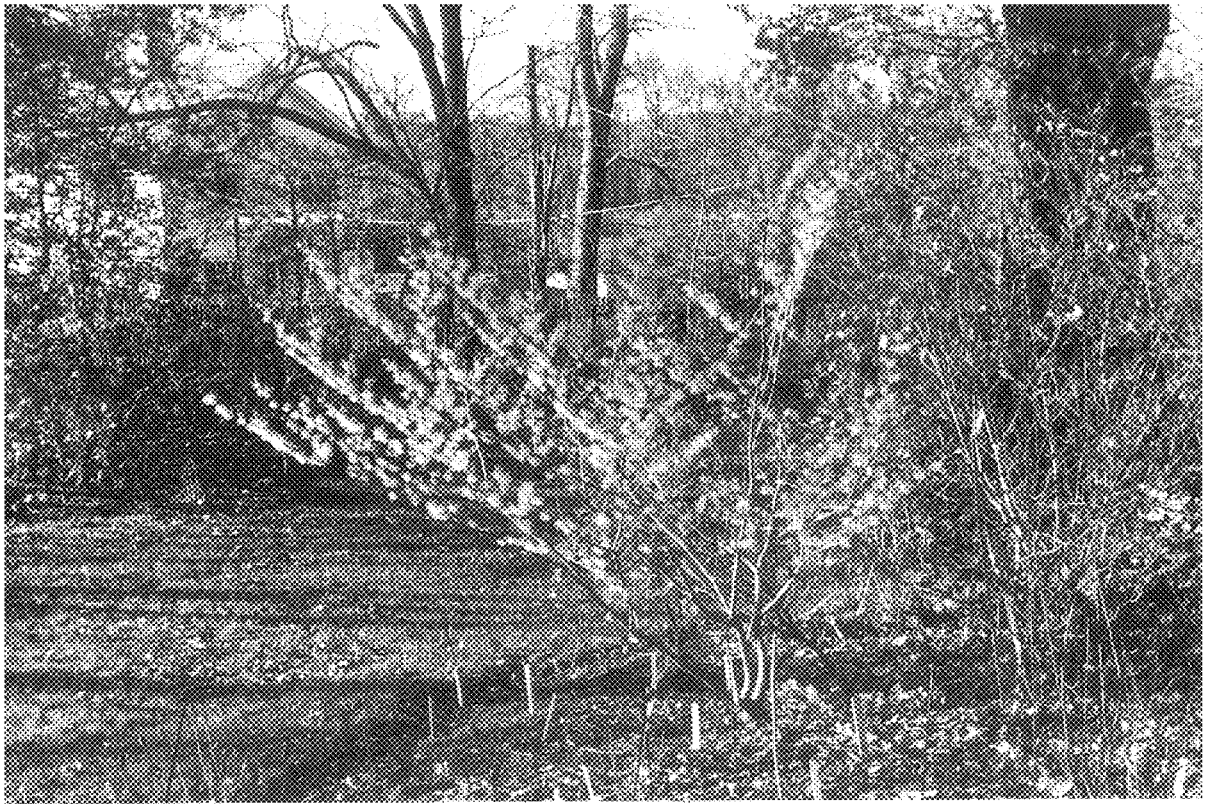
FIG. 2 is a view of the entire shrub.

Where originated: In a cultivated area in Plainsboro Township, N.J.
When originated: 1984.
How originated: Seedling in a nursery row.
By who originated: William Flemer III.
When and how and where first propagated: First propagated by grafting on *Hamamelis virginiana* seedlings in February 1992.
Name and address of present owner: William Flemer III 323 Mapleton Road Princeton, N.J., 08540-9605.
Where specimens described were grown: In Plainsboro Township, N.J.
Parentage:
Seed parent: *Hamamelis virginiana.*
Pollen parent: Unknown.
Newly found seedling of: *Hamamelis virginiana.*
Shrub:
- *Growth.*—Vigorous, upright, branching, spreading.
- *Height.*—2½ meters at maturity.
- *Spread.*—Dense and spreading; 2½ meters at maturity.
- *Hardiness.*—Very cold hardy, to −15° F.

Trunk: Old Stems — Stocky, smooth, diameter 5.5 cm measured 6 cm above ground Munsell light olive gray 7.5 Y 5/5.
Branches: Slender, smooth.
- *Crotch angle.*—40°.
- *Color.*—Munsell moderate brown 7.5 YR 4/5.
- *Lenticels.*—Small, abundant 1 mm wide; Munsell strong yellowish brown 10 YR 5/6.
- *Number.*—10 to 12 per 1 cm. of twig length.
- *Size.*—1 year branches approximately 0.5 cm in diameter and approximately 22 cm long.

Leaves:
- *Quantity.*—Abundant; average about 9 leaves per branch.
- *Arrangement.*—Alternate.

*Length.*—10 to 12 cm.
*Width.*—7 to 9 cm.
*Shape.*—Ovate, with unequally cuneate base with 8 to 9 alternate veins on each side of the central vein; apex is acuminate.
*Color.*—Fall color: upper surface — Munsell strong orange yellow 7.5 YR 7/11 lower surface Munsell dark orange yellow 10 YR 6/8.
*Thickness.*—Thin.
*New foliage color.*—Upper side — Munsell moderate olive green 7.5 GY 4/4. Under side — Munsell strong yellow green 2.5 GY 5/5.
*Mature foliage color.*—Upper surface — Munsell moderate olive green 5 GY 4/3. Lower surface — Munsell moderate yellow green 5 GY 5/6.
*Texture.*—Upper and under side-Smooth.
*Disease resistance.*—No observed foliage disease.
*Attitude.*—Horizontal.
*Margin.*—Serrate edge 12 to 16 blunt teeth on each side.
*Petiole.*—Short 1.5 cm. long. Diameter 2 mm. Color — Munsell strong yellow green 2.5 GY 6/8.
*Glands.*—None.
*Stipules.*—None.

Flower buds: Inconspicuous.
*Hardiness.*—Very hardy — not affected by hot weather.
*Size.*—0.3 mm. in diameter.
*Shape.*—Ovoid, nearly globular.
*Color.*—Munsell-strong yellowish brown 10 YR 5/6.
*Number.*—4.
*Length.*—3 mm.
*Color.*—Munsell Dark Red 2.5 R 3/7.
*Sepals.*—Smooth edge; "hood" above bud.
*Calyx.*—Shape — very small, 6 mm in width shallow cup. Size — small. Aspect — smooth. Odor — no special odor when rubbed.
*Peduncle.*—Length — very short, 2 mm long. Aspect — Smooth. Strength — stiff, inflexible. Opening — bud opens well. Not affected by adverse conditions.

Flowers:
*Dates first bloom.*—November 1.
*Full bloom.*—November 15.
*Quantity.*—Very Abundant about 30 to 35 flowers per branch; Borne in tight clusters of 3 to 4 flowers.
*Size.*—Large — 2½ times larger than ordinary *Hamamelis virginiana* flowers; length of each petal — 2 cm; width — 0.2 cm; diameter of 4 petaled flower — 4 cm.
*Borne.*—Several together in cluster borne in tight cluster of 3 to 4 flowers. Shape — rounded, flat, very abundant.
*Stems.*—Very short, strong stems length — 0.5 cm; diameter — 2 mm.
*Form.*—When first open — slightly cupped. Permanence — flattens at maturity.

Petalage:
*Number of petals.*—4 from a common base.
*Shape of petals.*—Long, very narrow, slightly twisted.
*Size of petals.*—Length: 2 cm. Width: 0.2 cm.
*Color.*—Munsell brilliant yellow 5Y 9/9.
*Texture.*—Smooth. Not affected by wet weather. Not affected by hot weather, it does not flower in hot weather.
*Appearance.*—Satiny inside and out.
*Arrangement.*—4 petaled, petals in opposite pairs.
*Petaloids in center.*—None.
*Persistence.*—Drop off cleanly in approximately 30 days after fading.
*Fragrance.*—Not fragrant.
*Lastingness.*—On the plant — very long, usually 30 days. As cut flower — fair.

Fruits: Oval, 2 valved capsule bearing 2 oblong shiny black seeds 1 cm long by 3 mm wide. When borne: summer from flowering the previous November, opening and dispersing in October.
*Abundance.*—Sparse.
*Size.*—1.2 cm. long.
*Color.*—Munsell — moderate olive brown 2.5Y 4/4.
*Variety.*—Fertile.
*Aspect.*—Minutely tomentose.
*Sepals.*—Caducous.

Reproductive organs:
*Stamens.*—4 in number. Anthers — very small 3 mm long. Color — Munsell pale orange yellow 7.5 YR 9/4. Arrangement — tucked in calyx.
*Filaments.*—Threads — very short. Color — Munsell pale orange yellow 7.5 YR 9/4.
*Pollen.*—Color — Munsell brilliant greenish yellow 7.5 Y 9/8.
*Pistil.*—Styles bunched. Length — very short 3 mm long.
*Ovaries.*—All enclosed in calyx.

What is claimed is:

1. A new cultivar of *Hamamelis virginiana* characterized by exceptionally large and abundant flowers borne in dense clusters closely spaced on slender twigs as shown and described herein.

* * * * *